United States Patent
Sams

(10) Patent No.: US 9,474,709 B2
(45) Date of Patent: Oct. 25, 2016

(54) NATURAL MOISTURIZING COMPOSITION FOR PROMOTION OF HEALING AND TREATMENT OF SKIN DISORDERS

(71) Applicant: Mignonette F. Sams, Mobile, AL (US)

(72) Inventor: Mignonette F. Sams, Mobile, AL (US)

(*) Notice: Subject to any disclaimer, the term of this patent is extended or adjusted under 35 U.S.C. 154(b) by 252 days.

(21) Appl. No.: 14/474,703

(22) Filed: Sep. 2, 2014

(65) Prior Publication Data

US 2016/0058690 A1  Mar. 3, 2016

(51) Int. Cl.
*A61K 36/00* (2006.01)
*A61K 8/92* (2006.01)
*A61K 8/98* (2006.01)
*A61Q 19/00* (2006.01)

(52) U.S. Cl.
CPC .............. *A61K 8/922* (2013.01); *A61K 8/925* (2013.01); *A61K 8/986* (2013.01); *A61K 8/987* (2013.01); *A61Q 19/00* (2013.01); *A61K 2800/70* (2013.01)

(58) Field of Classification Search
None
See application file for complete search history.

(56) References Cited

U.S. PATENT DOCUMENTS

| | | | |
|---|---|---|---|
| 7,060,306 B2 | 6/2006 | Springstead |
| 7,887,857 B1 | 2/2011 | Johnson |
| 8,075,901 B1 | 12/2011 | Waters |
| 8,563,048 B2 | 10/2013 | Magee |
| 8,623,335 B2 | 1/2014 | Waddington |
| 2006/0269507 A1 | 11/2006 | Fuller |
| 2009/0155325 A1 | 6/2009 | Wenzel |
| 2009/0220616 A1 | 9/2009 | Joseph |
| 2010/0021563 A1 | 1/2010 | Levesque |
| 2011/0142954 A1 | 6/2011 | Koelzer |
| 2012/0204894 A1 | 8/2012 | Odoms |
| 2012/0324735 A1 | 12/2012 | Eagleton |
| 2013/0108599 A1 | 5/2013 | Comeaux |
| 2014/0127315 A1 | 5/2014 | Brown |

FOREIGN PATENT DOCUMENTS

CN          103202782 A  *  7/2013

* cited by examiner

*Primary Examiner* — Qiuwen Mi
(74) *Attorney, Agent, or Firm* — Adamsip, LLC; J. Hunter Adams; Stephen Thompson

(57) ABSTRACT

A preferred embodiment of a version of the invention is directed to a skin moisturizing composition for the treatment of a variety of skin disorders, including eczema, psoriasis, scleroderma, and similar skin conditions. The composition is comprised of a balm comprised of a base of shea butter and coconut oil. The composition may also be formulated as a cream or a soap. All of the formulations are comprised of natural ingredients that do not cause adverse side effects. All of the formulations may be used daily as moisturizers to promote smooth, healthy skin.

4 Claims, No Drawings

NATURAL MOISTURIZING COMPOSITION FOR PROMOTION OF HEALING AND TREATMENT OF SKIN DISORDERS

FIELD OF THE INVENTION

The present invention refers generally to a skin moisturizing composition for the promotion of healing of dry, irritated skin and the treatment of skin disorders and, more specifically, a moisturizing composition for the treatment of dry skin, eczema, psoriasis, scleroderma, and similar skin conditions.

BACKGROUND

Many different types of skin disorders affect human skin. Some examples include eczema, psoriasis, and scleroderma. Other examples of temporary or chronic skin conditions may include dry skin, rashes, skin discoloration, allergic reactions, sunburn, or similar problems. The symptoms of such skin conditions may range in severity from relatively mild to very severe.

Skin conditions are often treated with some type of moisturizing composition. However, many of the moisturizing compositions that are commercially available contain various synthetic ingredients. Such ingredients may cause skin irritation, particularly in people with sensitive skin, or even allergic reactions, thereby compounding the problem. In addition, many of the commercially available moisturizing compositions are ineffective in treating more serious conditions such as eczema, psoriasis, and scleroderma.

Therefore, there exists a need in the art for a moisturizing composition for topical application to the skin which is comprised of natural ingredients and is effective for treating a wide variety of skin conditions, including eczema, psoriasis, scleroderma, skin discoloration, dry skin, rashes, and similar temporary or chronic skin conditions. Furthermore, there exists a need in the art for a moisturizing composition comprised of natural ingredients which is effective for preventing a wide variety of skin conditions by nourishing and softening the skin and promoting smooth, healthy skin.

SUMMARY

A preferred embodiment of a version of the invention is directed generally to a skin moisturizing composition for topical application to the skin. More specifically, a preferred embodiment of the invention is directed to a skin moisturizing composition that is effective for the treatment and/or prevention of symptoms of a wide variety of skin conditions, including, but not limited to, dry skin, eczema, psoriasis, scleroderma, and skin discoloration. The moisturizing composition is comprised of natural ingredients that nourish the skin and promote smooth, healthy skin.

In a preferred embodiment, the moisturizing composition comprises a balm. The balm is comprised of a base compound comprised of shea butter and coconut oil. In a preferred embodiment, the balm is comprised of about 30%-35% by weight of each of the ingredients shea butter and coconut oil. The balm is further comprised of at least one additional plant-based oil, and preferably a mixture of additional plant-based oils. In another preferred embodiment, the mixture of plant-based oils is comprised of safflower oil, olive oil, sweet almond oil, tea tree oil, jojoba oil, avocado oil, apricot oil, castor oil, peppermint oil, grapeseed oil, neem oil, and palm oil. In yet another preferred embodiment, the balm further comprises honey, vitamin E, vitamin D, vitamin C, aloe vera, rose water, garlic, glycerin, lecithin, lanolin, and emu oil.

The moisturizing composition may also be formulated as a cream or a soap. The balm serves as a starting material for producing the other formulations of the moisturizing composition. For instance, the cream is comprised of a quantity of the balm and a quantity of beeswax. The soap is comprised of a quantity of the balm, an additional quantity of coconut oil, an additional quantity of olive oil, a quantity of goat's milk, and a quantity of lye.

The moisturizing composition of the present invention has been found to have superior and unexpected properties when applied to the skin of a person suffering from a variety of skin conditions. The composition is particularly effective in treating eczema, psoriasis, and scleroderma. Although many of the particular ingredients found in the present invention are known for use in other moisturizing products, it is the unique combination of ingredients found in the present invention that provide the superior and unexpected properties of the present composition.

Accordingly, an object of the present invention is to provide a moisturizing composition. The composition may be formulated as a balm, a cream, or a soap. Another object of the present invention is to provide a moisturizing composition that is effective in treating eczema, psoriasis, and scleroderma, as well as more common skin conditions such as dry skin, skin discoloration, rashes, and sunburn. Furthermore, it is yet another object of the present invention to provide a moisturizing composition that can be used regularly to nourish and soften skin and to promote smooth, healthy skin. It is additionally an object of the present invention to provide a moisturizing composition comprised of natural ingredients that do not cause any adverse side effects.

These and other features, aspects, and advantages of the present invention will become better understood with reference to the following description and appended claims.

DETAILED DESCRIPTION

In the Summary above and in this Detailed Description, and the claims below, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, ingredients, steps, etc. are optionally present. For example, an article "comprising" components A, B, and C can contain only components A, B, and C, or can contain not only components A, B, and C, but also one or more other components.

Where reference is made herein to a method comprising two ore more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

As used herein, the terms "about" or "approximately" mean within an acceptable range of a given concentration of a given substance as determined by one having ordinary skill in the art. For instance, depending on the method by which a given concentration is measured, the terms "about" or "approximately" may include a range of up to 10% of a given concentration.

As used herein, the term "plant-based oil" refers to any type of oil derived from any plant source. This term may include, but is not limited to, safflower oil, olive oil, sweet almond oil, tea tree oil, jojoba oil, avocado oil, apricot oil, castor oil, peppermint oil, grapeseed oil, neem oil, or palm oil.

Turning now to the present invention, a preferred embodiment relates to a skin moisturizing composition for treating various skin conditions and disorders, including, but not limited to, eczema, psoriasis, scleroderma, dry skin, rashes, skin discoloration, allergic reactions, and minor burns including sunburn.

The moisturizing composition can be formulated as a balm, a cream, or a soap. The balm serves as a starting material from which the other formulations may be produced.

The balm is comprised of a base compound comprising shea butter and coconut oil. In a preferred embodiment, the balm is comprised of about 30%-35% by weight of each of the ingredients shea butter and coconut oil. Thus the base generally comprises about 60%-70% of the balm by weight. The balm is further comprised of at least one additional plant-based oil, and preferably of a mixture of plant-based oils. In a preferred embodiment, the mixture of plant-based oils is comprised of safflower oil, olive oil, sweet almond oil, tea tree oil, jojoba oil, avocado oil, apricot oil, castor oil, peppermint oil, grapeseed oil, neem oil, and palm oil. The concentration of each of these ingredients in the balm can range from about 1%-2% by weight. In a preferred embodiment, the concentration of each of the plant-based oils is approximately equal.

In another preferred embodiment, the balm further comprises honey, vitamin E, vitamin D, vitamin C, aloe vera, rose water, garlic, glycerin, lecithin, lanolin, and emu oil. The concentration of each of these ingredients in the balm can range from about 1%-2% by weight. In a preferred embodiment, the concentration of each of these ingredients is approximately equal.

In the most preferred embodiment of the invention, the balm is comprised of about 30% by weight shea butter, about 30% by weight coconut oil, and about 1.7%-1.8% by weight of each of the following ingredients: safflower oil, olive oil, sweet almond oil, tea tree oil, jojoba oil, avocado oil, apricot oil, castor oil, peppermint oil, grapeseed oil, neem oil, palm oil, honey, vitamin E, vitamin D, vitamin C, aloe vera, rose water, garlic, glycerin, lecithin, lanolin, and emu oil.

To prepare the balm, the shea butter and coconut oil are mixed and heated to approximately 70 to 80 degrees Fahrenheit. The heated mixture is stirred until homogeneous and then removed from the heat. While the mixture is still warm, all other ingredients are added and the mixture is stirred until homogenous. Once the mixture is homogeneous, it is allowed to cool. After cooling, the balm is ready for use.

As noted above, the balm serves as a starting material for making a moisturizing cream or a moisturizing soap. The cream is comprised of a quantity of the balm and a quantity of beeswax. In a preferred embodiment, the cream is comprised of about 70%-90% by volume balm and about 10%-30% by volume beeswax. In another preferred embodiment, the cream is comprised of about 80% by volume balm and about 20% by volume beeswax.

To prepare the cream, a "double boiler" method is used. First, water is boiled in a pan or other suitable container. Next, the balm and the beeswax are added to a separate container, preferably a glass bowl. The glass bowl is then placed into the boiling water. In a preferred embodiment, about 8 fluid ounces (1 cup) of balm and about 4 tablespoons (¼ cup) of beeswax are added to the glass bowl. Once the balm and beeswax mixture is heated by the boiling water, the mixture is stirred until melted. Once melted, the bowl is removed from the heat and the contents are mixed until homogeneous. Once the mixture is homogeneous, it is allowed to cool. After cooling, the cream is ready for use.

The moisturizing composition may also be formulated as a soap. The soap is comprised of a quantity of balm, additional quantities of coconut oil and olive oil, a quantity of goat's milk, and a quantity of lye. In a preferred embodiment, the soap is comprised of about 8 fluid ounces of balm, about 17 fluid ounces of coconut oil, about 17 fluid ounces of olive oil, about 16 fluid ounces of goat's milk, and about 6 to 7 ounces (mass) of lye.

To prepare the soap, the following method is used. The balm, coconut oil, and olive oil are heated in a first container. The balm, coconut oil, and olive oil are then mixed until homogeneous. In a second container, also heated, the lye and goat's milk are added to the second container while being stirred. After the contents of each container have been mixed until homogeneous, each mixture is allowed to cool separately to the same temperature, preferably a temperature in a range between 55 and 75 degrees Celsius. When both mixtures have been cooled to the same temperature, the contents of each container are then mixed together until they reach "trace." Trace is achieved when the resulting mixture has reached a point of emulsification, meaning that the oils and water present in the mixture have completely mixed and will not separate from each other. Once trace has been reached, the mixture is placed in a mold and allowed to set for a minimum of 24 hours.

The balm and the cream may be used several times per day. These formulations are applied directly to the affected areas of skin. The soap is preferably used once per day. Each formulation is individually effective in treating various skin disorders and conditions, particularly eczema, psoriasis, and scleroderma. For maximum effectiveness, the balm or the cream can be applied to the affected area of skin immediately after the affected area is washed with the soap. Additionally, each formulation may be used to prevent or reduce the symptoms of various skin conditions. Each formulation may be used daily to nourish and soften the skin and promote smooth, healthy skin.

The moisturizing composition set forth in this description contains some ingredients previously known in the art. For instance, the two ingredients making up the base compound for the moisturizing balm (shea butter and coconut oil) are both known in the art as effective emollients when applied to skin. Coconut oil is an oil extracted from the meat of coconuts and is known to be a natural source of saturated fats. Because of its high saturated fat content, coconut oil is also known to be very stable and slow to oxidize, meaning the oil is not easily subject to rancidification. Shea butter is known not only as an emollient, but it is also known to have humectant and anti-inflammatory properties, as well. Both ingredients contain natural fats that are known to provide numerous benefits to the skin and that act as natural moisturizers to help soften skin.

The moisturizing composition is also comprised of essential oils known for their use in aromatherapy, including tea tree oil, peppermint oil, sweet almond oil, apricot oil, and neem oil. These essential oils help to enhance both the aesthetic qualities and the emollient properties of the moisturizing composition. Additionally, the composition is comprised of additional types of plant-based oils known to have emollient properties.

Although many of the particular ingredients described herein are known individually for their use in various moisturizing compounds, the unique combination of ingredients and the concentrations of said ingredients as set forth in this description provide superior and unexpected properties in the present invention compared to other moisturizing compositions. The moisturizing composition of the present invention is particularly effective in treating eczema, psoriasis, and scleroderma. However, the composition is also effective in treating dry skin, rashes, skin discoloration, allergic reactions, minor burns including sunburn, or any similar temporary or chronic skin conditions. Another advantage of the present invention is that the moisturizing composition is comprised of natural ingredients that do not cause adverse side effects and can be used on a daily basis to promote smooth, healthy skin.

For each formulation of the moisturizing composition described in this detailed description, the quantities of ingredients set forth are exemplary only and may be adjusted to produce the formulation on a commercial scale. The heating and mixing of ingredients may be done on a commercial scale by any suitable method known in the art.

The embodiments and formulations of the present invention disclosed herein will consist essentially of the ingredients as set forth in this Detailed Description. However, it should be noted that small amounts of other substances (for instance, substances having concentrations of less than about 1% by weight of the composition) may be present in the composition without significantly altering the effectiveness of any composition or formulation as described.

It is understood that versions of the invention may come in different forms and embodiments. Additionally, it is understood that one of skill in the art would appreciate these various forms and embodiments as falling within the scope of the invention as disclosed in the Detailed Description and the following claims.

What I claim as my invention is:

1. A skin moisturizing cream, comprising:
   a. about 30%-35% by weight shea butter;
   b. about 30%-35% by weight coconut oil;
   c. about 1%-2% by weight safflower oil;
   d. about 1%-2% by weight olive oil;
   e. about 1%-2% by weight sweet almond oil;
   f. about 1%-2% by weight tea tree oil;
   g. about 1%-2% by weight jojoba oil;
   h. about 1%-2% by weight avocado oil;
   i. about 1%-2% by weight apricot oil;
   j. about 1%-2% by weight castor oil;
   k. about 1%-2% by weight peppermint oil;
   l. about 1%-2% by weight grapeseed oil;
   m. about 1%-2% by weight neem oil; and,
   n. about 1%-2% by weight palm oil.

2. A skin moisturizing cream, comprising:
   a. about 30%-35% by weight shea butter;
   b. about 30%-35% by weight coconut oil;
   c. about 1%-2% by weight safflower oil;
   d. about 1%-2% by weight olive oil;
   e. about 1%-2% by weight sweet almond oil;
   f. about 1%-2% by weight tea tree oil;
   g. about 1%-2% by weight jojoba oil;
   h. about 1%-2% by weight avocado oil;
   i. about 1%-2% by weight apricot oil;
   j. about 1%-2% by weight castor oil;
   k. about 1%-2% by weight peppermint oil;
   l. about 1%-2% by weight grapeseed oil;
   m. about 1%-2% by weight neem oil;
   n. about 1%-2% by weight palm oil;
   o. about 1%-2% by weight honey;
   p. about 1%-2% by weight vitamin E;
   q. about 1%-2% by weight vitamin D;
   r. about 1%-2% by weight vitamin C;
   s. about 1%-2% by weight aloe vera;
   t. about 1%-2% by weight rose water;
   u. about 1%-2% by weight garlic;
   v. about 1%-2% by weight glycerin;
   w. about 1%-2% by weight lecithin;
   x. about 1%-2% by weight lanolin; and,
   y. about 1%-2% by weight emu oil.

3. A skin moisturizing cream, comprising:
   a. about 80% by volume of a skin moisturizing balm, said balm comprising:
      i. about 30%-35% by weight shea butter;
      ii. about 30%-35% by weight coconut oil;
      iii. about 1%-2% by weight safflower oil;
      iv. about 1%-2% by weight olive oil;
      v. about 1%-2% by weight sweet almond oil;
      vi. about 1%-2% by weight tea tree oil;
      vii. about 1%-2% by weight jojoba oil;
      viii. about 1%-2% by weight avocado oil;
      ix. about 1%-2% by weight apricot oil;
      x. about 1%-2% by weight castor oil;
      xi. about 1%-2% by weight peppermint oil;
      xii. about 1%-2% by weight grapeseed oil;
      xiii. about 1%-2% by weight neem oil;
      xiv. about 1%-2% by weight palm oil;
      xv. about 1%-2% by weight honey;
      xvi. about 1%-2% by weight vitamin E;
      xvii. about 1%-2% by weight vitamin D;
      xviii. about 1%-2% by weight vitamin C;
      xix. about 1%-2% by weight aloe vera;
      xx. about 1%-2% by weight rose water;
      xxi. about 1%-2% by weight garlic;
      xxii. about 1%-2% by weight glycerin;
      xxiii. about 1%-2% by weight lecithin;
      xxiv. about 1%-2% by weight lanolin; and,
      xxv. about 1%-2% by weight emu oil, and
   b. about 20% by volume beeswax.

4. A skin moisturizing soap, comprising:
   a. about 8 fluid ounces of a skin moisturizing balm, said balm comprising:
      i. about 30%-35% by weight shea butter;
      ii. about 30%-35% by weight coconut oil;
      iii. about 1%-2% by weight safflower oil;
      iv. about 1%-2% by weight olive oil;
      v. about 1%-2% by weight sweet almond oil;
      vi. about 1%-2% by weight tea tree oil;
      vii. about 1%-2% by weight jojoba oil;
      viii. about 1%-2% by weight avocado oil;
      ix. about 1%-2% by weight apricot oil;
      x. about 1%-2% by weight castor oil;
      xi. about 1%-2% by weight peppermint oil;
      xii. about 1%-2% by weight grapeseed oil;
      xiii. about 1%-2% by weight neem oil;
      xiv. about 1%-2% by weight palm oil;
      xv. about 1%-2% by weight honey;
      xvi. about 1%-2% by weight vitamin E;

xvii. about 1%-2% by weight vitamin D;
xviii. about 1%-2% by weight vitamin C;
xix. about 1%-2% by weight aloe vera;
xx. about 1%-2% by weight rose water;
xxi. about 1%-2% by weight garlic;
xxii. about 1%-2% by weight glycerin;
xxiii. about 1%-2% by weight lecithin;
xxiv. about 1%-2% by weight lanolin; and,
xxv. about 1%-2% by weight emu oil;
b. about 17 fluid ounces of coconut oil;
c. about 17 fluid ounces of olive oil;
d. about 16 fluid ounces of goat's milk; and,
e. about 6.5 ounces (mass) of lye.

\* \* \* \* \*